(12) United States Patent
Takahashi

(10) Patent No.: US 12,343,212 B2
(45) Date of Patent: Jul. 1, 2025

(54) ULTRASONIC DIAGNOSTIC APPARATUS AND IMAGE PROCESSING APPARATUS

(71) Applicant: CANON MEDICAL SYSTEMS CORPORATION, Otawara (JP)

(72) Inventor: Hiroki Takahashi, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 131 days.

(21) Appl. No.: 18/155,217

(22) Filed: Jan. 17, 2023

(65) Prior Publication Data

US 2023/0225710 A1    Jul. 20, 2023

(30) Foreign Application Priority Data

Jan. 18, 2022    (JP) ................................ 2022-005904

(51) Int. Cl.
    *A61B 8/00*    (2006.01)

(52) U.S. Cl.
    CPC .......... *A61B 8/5207* (2013.01); *A61B 8/4477* (2013.01)

(58) Field of Classification Search
    CPC ... A61B 8/5269; A61B 8/4488; A61B 8/5207; A61B 8/4477; A61B 8/488;

(Continued)

(56) References Cited

U.S. PATENT DOCUMENTS

| 6,309,356 B1* | 10/2001 | Ustuner | G01S 7/52026 |
| | | | 600/443 |
| 6,436,044 B1* | 8/2002 | Wang | G01S 7/52047 |
| | | | 600/443 |

(Continued)

FOREIGN PATENT DOCUMENTS

JP    2014-39702 A    3/2014

OTHER PUBLICATIONS

Matrone, Alessandro Stuart Savoia, Giosue Caliano, and GiovanniMagenes, "The Delay Multiply and Sum Beamforming Algorithm in Ultrasound B-Mode Medical Imaging", IEEE Transactions On Medical Imaging, vol. 34, No. 4, Apr. 2015. (Year: 2015).*

(Continued)

*Primary Examiner* — Jeffrey G Hoekstra
*Assistant Examiner* — Nicholas A Robinson
(74) *Attorney, Agent, or Firm* — Oblon, McClelland, Maier & Neustadt, L.L.P.

(57) ABSTRACT

An ultrasonic diagnostic apparatus according to an embodiment has transmitting and receiving circuitry that transmits and receives ultrasonic waves, and processing circuitry. The transmitting and receiving circuitry is configured to perform first beamforming processing on reflected wave signals output from a plurality of transducer elements that receive reflected waves and perform second beamforming processing different from the first beamforming processing on the reflected wave signals. The processing circuitry is configured to calculate an evaluation value of spatial correlation of the reflected wave signals and perform third beamforming processing based on a first processing result that is a processing result of the first beamforming processing, a second processing result that is a processing result of the second beamforming processing, and the evaluation value.

8 Claims, 5 Drawing Sheets

TRANSDUCER ELEMENT NUMBER

TRANSDUCER ELEMENT NUMBER

(58) Field of Classification Search
CPC ..... A61B 8/5246; A61B 8/54; G01S 7/52095; G01S 15/8911; G01S 7/52047; G01S 7/52077; G01S 15/8915; G10K 11/346; B06B 1/0215; B06B 2201/20; B06B 2201/76

See application file for complete search history.

(56) References Cited

U.S. PATENT DOCUMENTS

| | | | | |
|---|---|---|---|---|
| 2012/0004545 | A1* | 1/2012 | Ziv-Ari | A61B 8/0883 600/437 |
| 2014/0058262 | A1 | 2/2014 | Yoda | |
| 2021/0132223 | A1* | 5/2021 | Hennersperger | G01S 7/52049 |

OTHER PUBLICATIONS

Matrone, G., et al. "The Delay Multiply and Sum Beamforming Algorithm in Ultrasound B-Mode Medical Imaging", IEEE Transactions On Medical Imaging, vol. 34, No. 4, 2015, 11 pages.
https://www.youtube.com/watch?v=qhkFok9vDTs Retrieved Jan. 2023.
https://www.innervision.co.jp/sp/expo/products/philips_us_epiq_cvx Retrieved Jan. 2023.

* cited by examiner

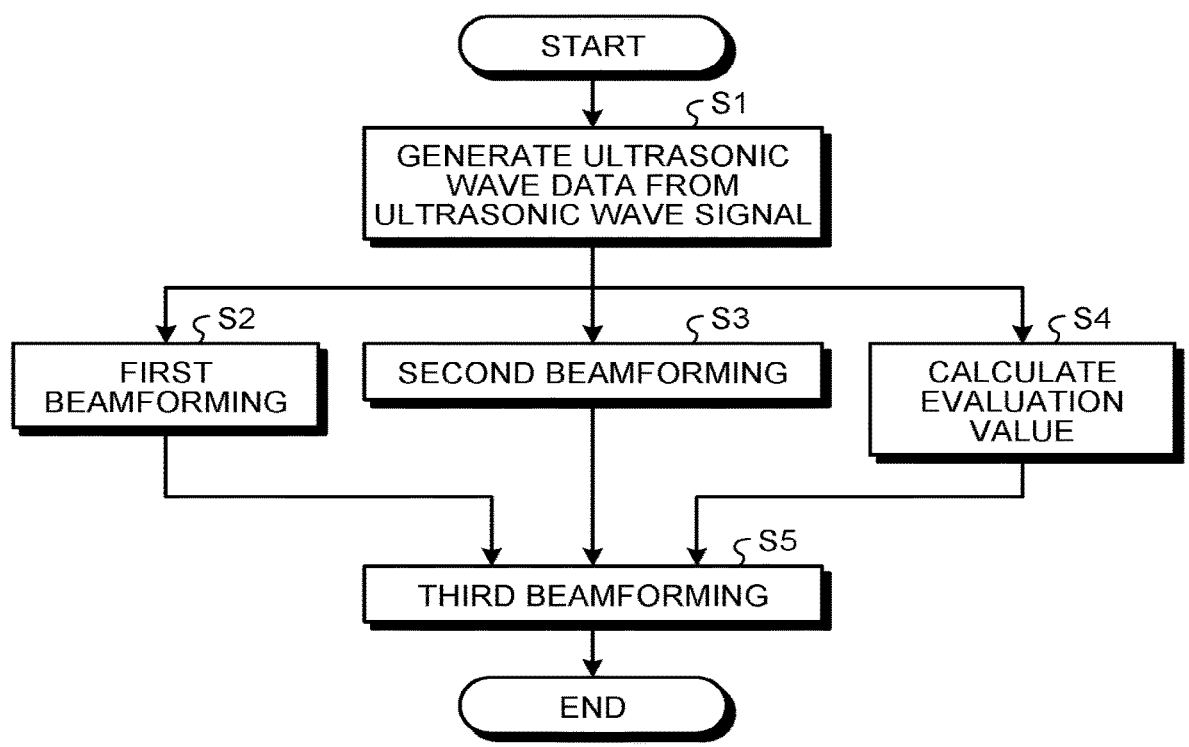

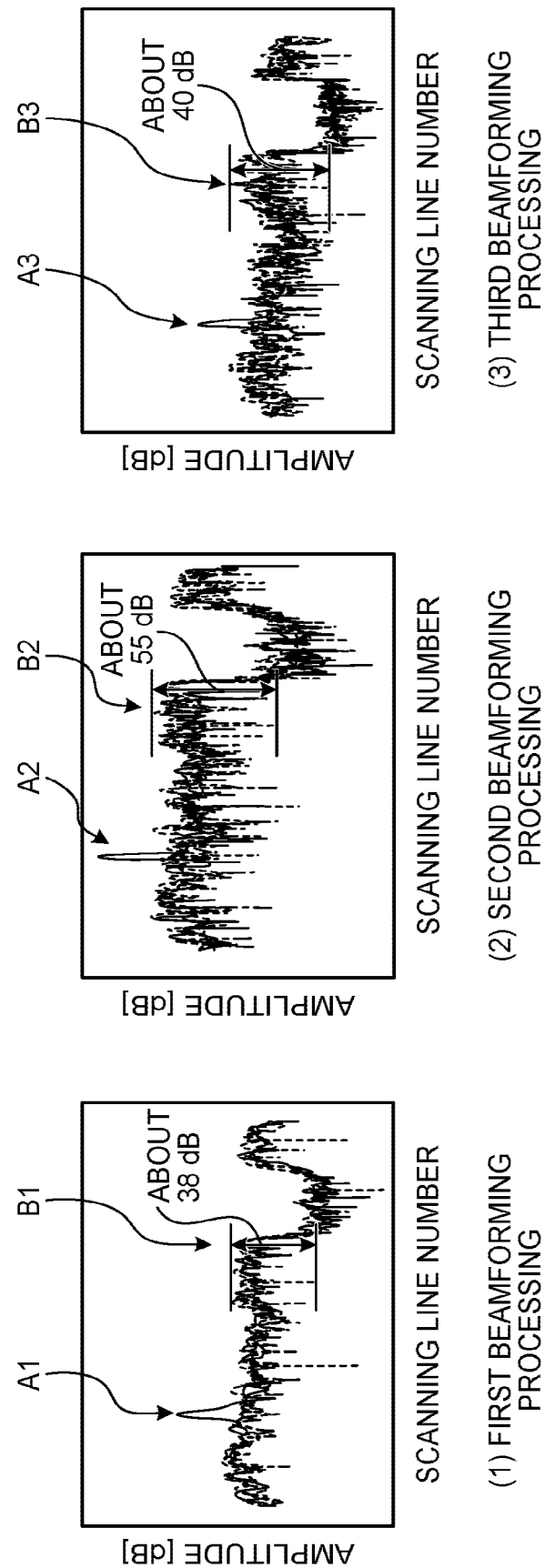

ULTRASONIC DIAGNOSTIC APPARATUS AND IMAGE PROCESSING APPARATUS

CROSS-REFERENCE TO RELATED APPLICATIONS

This application is based upon and claims the benefit of priority from Japanese Patent Application No. 2022-005904, filed on Jan. 18, 2022; the entire contents of which are incorporated herein by reference.

FIELD

An embodiment described herein relates generally to an ultrasonic diagnostic apparatus and an image processing apparatus.

BACKGROUND

A conventional ultrasonic diagnostic apparatus performs receiver beamforming using reflected wave signals received to improve an image resolution. The receiver beamforming has technologies called adaptive beamforming, such as a minimum variance method, a coherence factor beamforming method, and a delay-multiply-and-sum (DMAS) method. The adaptive beamforming, however, may degrade a contrast resolution and contrast-to-noise ratio in accordance with a spatial correlation of reflected wave signals. The adaptive beamforming, on the other hand, may be suitable in accordance with a spatial correlation of reflected wave signals.

BRIEF DESCRIPTION OF THE DRAWINGS

FIG. 5 is a diagram illustrating an example of beamforming processing performed by the ultrasonic diagnostic apparatus according to the present embodiment; and FIG. 6 is a diagram illustrating examples of amplitude profile of an image generated by each beamforming processing.

DETAILED DESCRIPTION

An ultrasonic diagnostic apparatus and an image processing apparatus according to an embodiment will be described in the following, with reference to the accompanying drawings. In the following embodiment, portions with the same reference signs are assumed to operate in the same way, and duplicate explanations are omitted, as appropriate.

Figure 1:
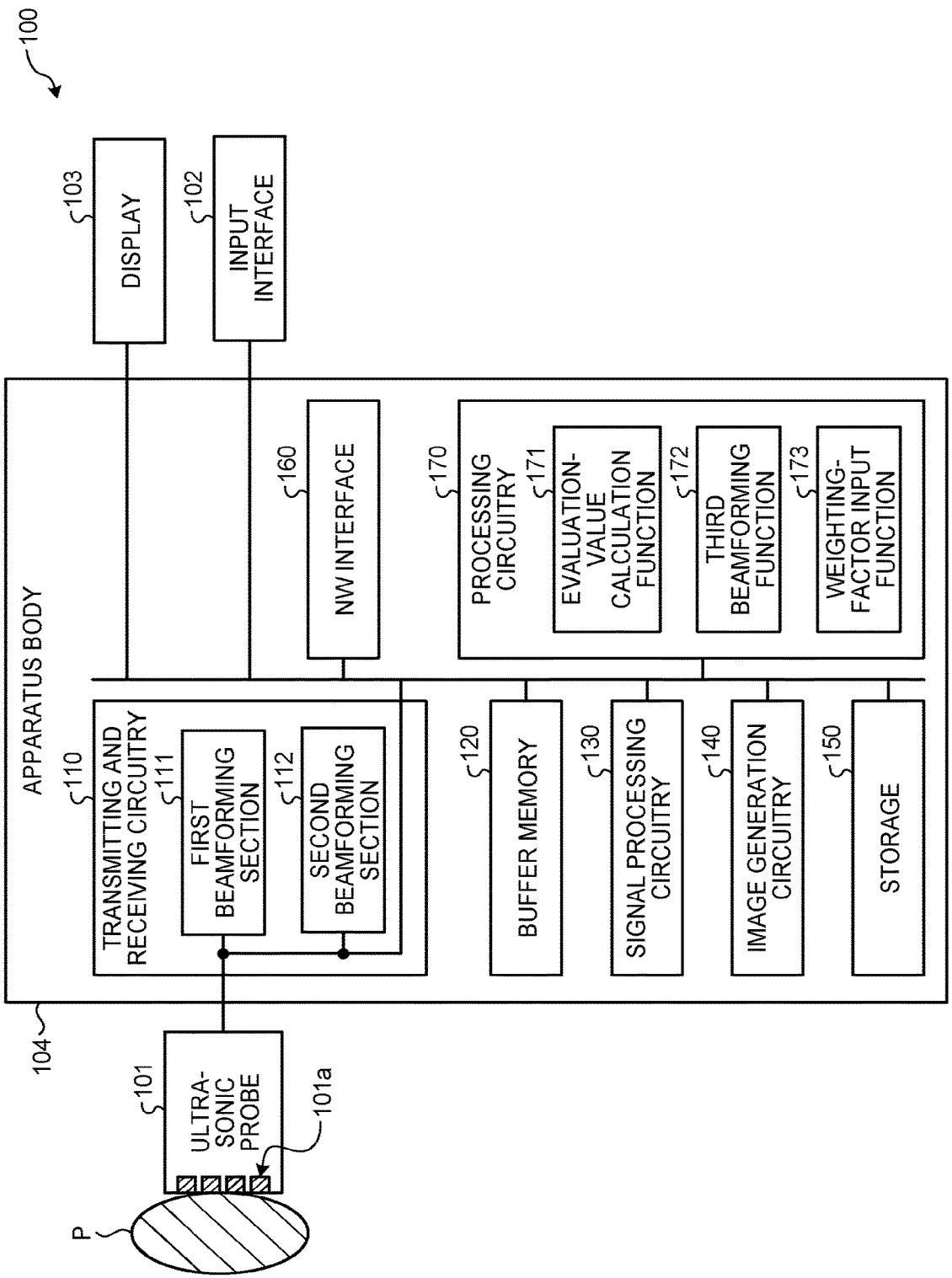
FIG. 1 is a block diagram illustrating a configuration example of an ultrasonic diagnostic apparatus according to a present embodiment.

FIG. 1 is a block diagram illustrating a configuration example of an ultrasonic diagnostic apparatus 100 according to the present embodiment. As illustrated in FIG. 1, the ultrasonic diagnostic apparatus 100 has an ultrasonic probe 101, an input interface 102, a display 103, and an apparatus body 104. The ultrasonic probe 101, the input interface 102, and the display 103 are communicatively connected to the apparatus body 104. The ultrasonic diagnostic apparatus 100 is one example of an ultrasonic diagnostic apparatus and an image processing apparatus.

The ultrasonic probe 101 has a plurality of transducer elements 101a, and the transducer elements 101a generate ultrasonic waves based on drive signals supplied from transmitting and receiving circuitry 110 that the apparatus body 104 has. The ultrasonic probe 101 receives reflected waves from a subject P and converts the reflected waves into electrical signals. The ultrasonic probe 101 is connected to the apparatus body 104 in a detachable manner.

When ultrasonic waves are transmitted from the ultrasonic probe 101 to the subject P, the transmitted ultrasonic waves are reflected one after another at discontinuous surfaces of acoustic impedance in the body tissue of the subject P and are received as reflected wave signals by the transducer elements 101a that the ultrasonic probe 101 has. The amplitude of the reflected wave signal received depends on the difference in acoustic impedance at the surface of discontinuity on which the ultrasonic wave is reflected. The reflected wave signal when a transmitted ultrasonic pulse is reflected by a surface such as a moving bloodstream or cardiac wall undergoes a frequency shift that depends on the velocity component with respect to the direction of ultrasonic transmission of a moving object due to the Doppler effect.

The form of the ultrasonic probe 101 does not matter in particular, and any form of the ultrasonic probe may be used. For example, the ultrasonic probe 101 may be a 1D array probe that scans the subject P two-dimensionally. The ultrasonic probe 101 may be a mechanical 4D probe or a 2D array probe that scan the subject P three-dimensionally.

The input interface 102 receives input operations of various instructions and information from an operator. Specifically, the input interface 102 converts input operations received from the operator into electrical signals and outputs the electrical signals to processing circuitry 170 of the apparatus body 104. For example, the input interface 102 is implemented with a trackball, a switch button, a mouse, a keyboard, a touchpad for which input operation is performed by touching the operating surface, a touchscreen in which a display screen and a touchpad are integrated, non-contact input circuitry using an optical sensor, voice input circuitry, and the like. The input interface 102 is not limited only to those provided with physical operating components such as a mouse, a keyboard, and the like. Examples of the input interface 102 also include processing circuitry for electrical signals that receives electrical signals corresponding to input operations from an external input device installed separately from the apparatus and outputs these electrical signals to control circuitry, for example.

The display 103 displays various information and images. Specifically, the display 103 converts the information and image data sent from the processing circuitry 170 into electrical signals for display to output these signals. For example, the display 103 is implemented by a liquid-crystal display monitor, a cathode ray tube (CRT) monitor, a touch panel, and the like. The output device that the ultrasonic diagnostic apparatus 100 is provided with is not limited to the display 103 and the ultrasonic diagnostic apparatus 100 may also be provided with a speaker, for example. The speaker outputs a predetermined sound of a beep and the like to notify the operator of the processing status of the apparatus body 104, for example.

The apparatus body 104 is a device that generates ultrasonic images based on reflected wave signals that the ultrasonic probe 101 has received. For example, the apparatus body 104 generates two-dimensional ultrasonic images based on two-dimensional reflected wave data that the ultrasonic probe 101 has received. The apparatus body 104 further generates three-dimensional ultrasonic images based on three-dimensional reflected wave data that the ultrasonic probe 101 has received.

The apparatus body 104 has, as illustrated in FIG. 1, the transmitting and receiving circuitry 110, a buffer memory 120, signal processing circuitry 130, image generation circuitry 140, a storage 150, a network (NW) interface 160, and the processing circuitry 170. The transmitting and receiving circuitry 110, the buffer memory 120, the signal processing circuitry 130, the image generation circuitry 140, the storage 150, the NW interface 160, and the processing circuitry 170 are communicatively connected to each other.

The transmitting and receiving circuitry 110 has a pulse generator, a transmission delay section, a pulser, and the like and supplies drive signals to the ultrasonic probe 101. The pulse generator repeatedly generates rate pulses at a predetermined rate frequency to form a transmitting ultrasonic wave. The transmission delay section gives a delay time for each transducer element 101a needed to focus the ultrasonic waves generated from the ultrasonic probe 101 into a beam shape and to determine transmission directivity to each rate pulse generated by the pulse generator. The pulser applies a drive signal (drive pulse) to the ultrasonic probe 101 at the timing based on the rate pulse. That is, the transmission delay section adjusts as desired the transmission direction of ultrasonic waves transmitted from the transducer element surface by varying the delay time given to each rate pulse.

The transmitting and receiving circuitry 110 has a preamplifier, an analog to digital (A/D) converter, quadrature detection circuitry, and the like, and generates reflected wave data by performing various processing on the reflected wave signals that the ultrasonic probe 101 has received.

The preamplifier amplifies the reflected wave signal for each channel to perform gain adjustment (gain correction). The A/D converter converts the gain-corrected reflected wave signal into a digital signal, by A/D converting the gain-corrected reflected wave signal. The quadrature detection circuitry converts the A/D-converted reflected wave signal into an in-phase signal (I signal, I: in-phase) and a quadrature signal (Q signal, Q: quadrature-phase) in the baseband.

The quadrature detection circuitry outputs the I signal and the Q signal as reflected wave data. In the following description, the I signal and the Q signal are referred to as IQ signals when collectively referred to. The IQ signals are also referred to as IQ data because they are A/D-converted digital data.

The transmitting and receiving circuitry 110, which transmits and receives ultrasonic waves, is provided with a first beamforming section 111 and a second beamforming section 112.

The first beamforming section 111 performs beamforming processing on the reflected wave signals received by the transducer elements 101a that receive reflected waves. For example, the first beamforming section 111 performs beamforming processing in a phase-additive method in which a delay time according to the timing at which each of the transducer elements 101a receives a reflected wave from the point of interest is given to the corresponding reflected wave signal and the reflected wave signals are added up. The point of interest is the object to which the transducer element 101a transmits ultrasonic wave.

In more detail, the first beamforming section 111 performs the beamforming processing in the phase-additive method on the reflected wave data generated from the reflected wave signal. The first beamforming section 111 gives the delay time needed to determine reception directivity. For example, when the distance to a reflector R (see FIG. 3) included in the subject P is different, the transducer elements 101a differ in the timing of receiving the reflected wave. Consequently, the first beamforming section 111 gives the delay time to the reflected wave data from each of the transducer elements 101a. Thus, the first beamforming section 111 matches the phase of each reflected wave data.

Furthermore, the first beamforming section 111 adds up a plurality of pieces of reflected wave data to which the delay time has been given. The first beamforming section 111 emphasizes, by adding up the reflected wave data, the reflected components from the direction corresponding to the reception directivity of the reflected wave data and forms a comprehensive beam of ultrasonic waves by the reception directivity and transmission directivity.

The second beamforming section 112 performs second beamforming processing different from the first beamforming processing on the reflected wave signals that the transducer elements 101a have received. For example, the second beamforming section 112 performs the second beamforming processing in which a delay time according to the timing at which each of the transducer elements 101a receives a reflected wave from the point of interest is given to the corresponding reflected wave signal and the amplitude is adjusted with a reflected wave signal output by another transducer element 101a different from the transducer element 101a that has output the relevant reflected wave signal.

Figure 2:
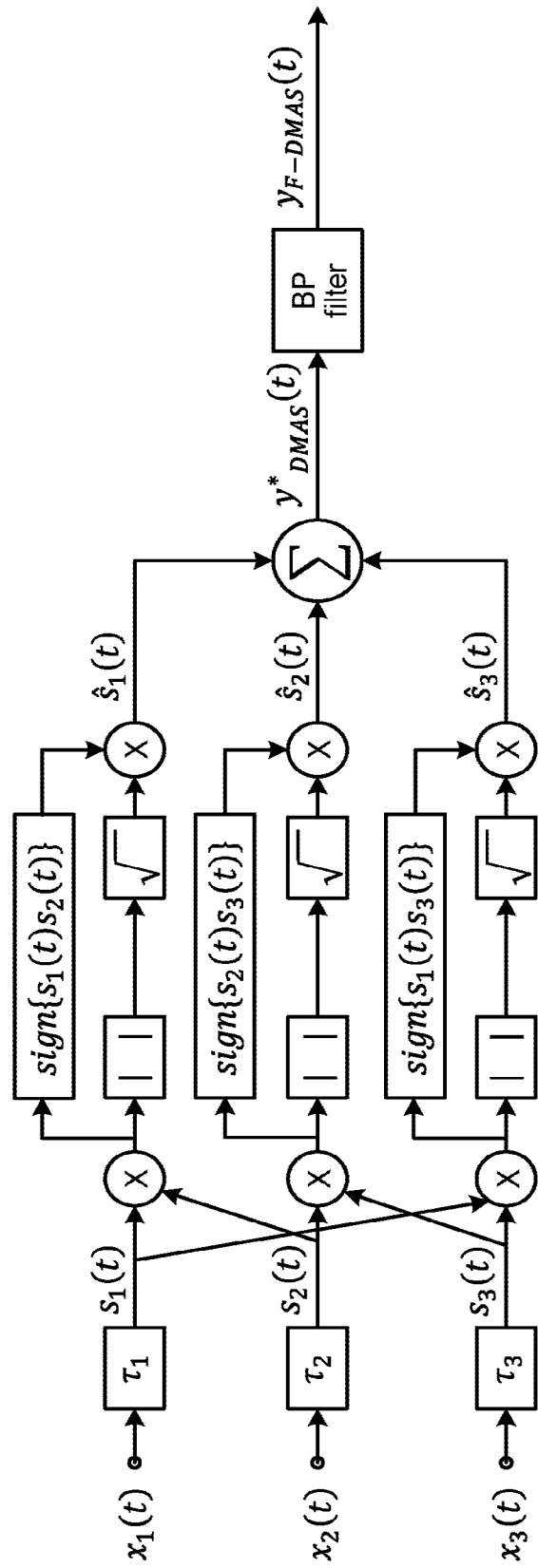
FIG. 2 is a configuration diagram illustrating a configuration example of a second beamforming section.

For example, the second beamforming section 112 performs the second beamforming processing that is adaptive beamforming processing in a delay-multiply-and-sum (DMAS) method, which is described in the following Non-Patent Literature: Giulia Matrone, Alessandro Stuart Savoia, Giosue Caliano, and Giovanni Magenes, "The Delay Multiply and Sum Beamforming Algorithm in Ultrasound B-Mode Medical Imaging", IEEE Transactions On Medical Imaging, Vol. 34, No. 4, April 2015. FIG. 2 is a configuration diagram illustrating a configuration example of the second beamforming section 112. As illustrated in FIG. 2, a delay time $\tau_i$ needed to determine the reception directivity is given to a reflected wave signal $x_i(t)$ (where i is a transducer element number) output from each transducer element 101a and the reflected wave signal is converted to a signal $s_i(t)$.

The second beamforming section 112 further performs, on the signal $s_i(t)$ corresponding to each transducer element 101a, processing of adjusting the amplitude with reflected wave data generated from a reflected wave signal output by another transducer element 101a different from the transducer element 101a that has output the reflected wave signal on which this reflected wave data was based. That is, the second beamforming section 112 multiplies the reflected wave data from one transducer element 101a by the amplitude of the reflected wave data of another different transducer element 101a to obtain $s_i(t)\,s_j(t)$. The second beamforming section 112 also calculates the square root of the absolute value $s_i(t)\,s_j(t)$. The second beamforming section 112 then integrates the sign $(s_i(t)\,s_j(t))$ of $s_i(t)\,s_j(t)$ with respect to the calculated square root of the absolute value $s_i(t)\,s_j(t)$ to calculate $\hat{s}_{ij}(t)$. This is expressed by Expression 1.

$$\hat{s}_{ij}(t) = \mathrm{sign}(s_i(t)s_j(t)) \cdot \sqrt{|s_i(t)s_j(t)|}. \tag{1}$$

The second beamforming section 112 further adds up $s_{ij}(t)$ across the transducer elements 101a to calculate $Y^*_{DMAS}(t)$. This is expressed by Expression 2. In Expression 2, i and j represent the transducer element 101a number and N represents the total number of the transducer elements 101a.

$$y^*_{DMAS}(t) = \sum_{i=1}^{N-1} \sum_{j=i+1}^{N} \hat{s}_{ij}(t) = \sum_{n=1}^{} \hat{s}_n(t). \quad (2)$$

As a result, in the second beamforming section 112, the reflected component from the direction corresponding to the reception directivity of the reflected wave data is emphasized, and the comprehensive beam of ultrasonic wave is formed by the reception directivity and transmission directivity. The second beamforming section 112 also multiplies the amplitude of the other reflected wave data and increases the number of additions, so that the amplitude of a higher amplitude portion is more increased and the amplitude of a lower amplitude portion is more subdued.

Then, the transmitting and receiving circuitry 110 causes the buffer memory 120 to store the reflected wave data for which no beamforming processing has been performed, the reflected wave data that is the processing result of the first beamforming processing, and the reflected wave data that is the processing result of the second beamforming processing.

The second beamforming section 112 is not limited to performing the adaptive beamforming processing in the DMAS method but may perform adaptive beamforming processing in a minimum variance method, adaptive beamforming processing in a coherence factor beamforming method, or adaptive beamforming processing of other methods. The minimum variance method is a method that increases the spatial resolution by multiplying the input ultrasonic signal by a coefficient that corresponds to the signal. The coherence factor beamforming method is a method that enhances spatial resolution by weighting the reflected ultrasonic signal using a phase coherence factor obtained from the phase variance of the received ultrasonic signal.

The buffer memory 120 is implemented, for example, with a semiconductor memory element such as a random access memory (RAM), a flash memory, or the like. The buffer memory 120 stores therein the reflected wave data output from the transmitting and receiving circuitry 110. In more detail, the buffer memory 120 stores therein the reflected wave data for which no beamforming processing has been performed, the reflected wave data that is the processing result of the first beamforming processing, and the reflected wave data that is the processing result of the second beamforming processing.

The buffer memory 120 further stores therein the reflected wave data generated by a third beamforming function 172.

The signal processing circuitry 130 acquires the reflected wave data that is generated by the third beamforming function 172 stored in the buffer memory 120. The signal processing circuitry 130 performs logarithmic amplification, envelope detection processing, and the like on the reflected wave data acquired from the buffer memory 120 to generate data (B-mode data) in which the signal strength is expressed in terms of brightness in luminance. The signal processing circuitry 130 performs frequency analysis on the velocity information from the reflected wave data acquired from the buffer memory 120, extracts bloodstream, tissue, and contrast agent echo components due to the Doppler effect and generates data (Doppler data) for which moving object information such as velocity, variance, and power is extracted on multiple points.

The signal processing circuitry 130 is capable of processing both two-dimensional reflected wave data and three-dimensional reflected wave data. That is, the signal processing circuitry 130 generates two-dimensional B-mode data from two-dimensional reflected wave data and generates three-dimensional B-mode data from three-dimensional reflected wave data. The signal processing circuitry 130 further generates two-dimensional Doppler data from two-dimensional reflected wave data and generates three-dimensional Doppler data from three-dimensional reflected wave data.

The image generation circuitry 140 generates ultrasonic images from the data generated by the signal processing circuitry 130. For example, the image generation circuitry 140 generates a two-dimensional B-mode image, for which the intensity of the reflected wave is expressed in terms of luminance, from the two-dimensional B-mode data generated by the signal processing circuitry 130.

For example, the image generation circuitry 140 generates a two-dimensional Doppler image, for which bloodstream information is visualized, from the two-dimensional Doppler data generated by the signal processing circuitry 130. A two-dimensional Doppler image is velocity image data representing the average velocity of the bloodstream, variance image data representing the variance value of the bloodstream, power image data representing the power of the bloodstream, or image data of a combination of the foregoing. The image generation circuitry 140 generates, as a Doppler image, a color Doppler image for which bloodstream information such as average velocity, variance value, and power of bloodstream is displayed in color, or a Doppler image for which one of bloodstream information is displayed in grayscale.

For example, the image generation circuitry 140 is capable of also generating an M-mode image from the time-series data of B-mode data on a single scanning line generated by the signal processing circuitry 130. The image generation circuitry 140 is capable of also generating Doppler waveforms, for which velocity information on bloodstream and tissue is plotted along time series, from the Doppler data generated by the signal processing circuitry 130.

In this case, the image generation circuitry 140, in general, converts (scan-converts) the scanning line signal stream of ultrasonic scanning into a scanning line signal stream of video format typical of television and the like and generates an ultrasonic image for display. Specifically, the image generation circuitry 140 performs coordinate transformations according to the ultrasonic scanning form with the ultrasonic probe 101, thereby generating ultrasonic images for display. The image generation circuitry 140 further performs, as other various image processing in addition to the scan conversion, image processing to regenerate a mean value image of luminance using a plurality of image frames after scan conversion (smoothing processing), image processing using a differential filter in the image (edge enhancement processing), and the like, for example. In addition, the image generation circuitry 140 synthesizes text information on various parameters, scales, body marks, and the like into the ultrasonic image data.

That is, the B-mode data and the Doppler data are the data before the scan conversion processing, and the data generated by the image generation circuitry 140 is the image data for display after the scan conversion processing. In the following description, the data (B-mode data and Doppler data) before the scan conversion processing is also referred to as "RAW data".

The image generation circuitry 140 generates two-dimensional B-mode images and two-dimensional Doppler images that are two-dimensional ultrasonic images from two-dimensional B-mode data and two-dimensional Doppler data that are RAW data. The image generation circuitry 140 can also generate a superimposed image for which a color Doppler image is superimposed on a two-dimensional B-mode image, for example.

The storage 150 stores therein various types of data. For example, the storage 150 stores therein control programs to perform ultrasonic transmission and reception, image processing, and display processing, and various data such as diagnostic information (for example, patient ID, physician's findings, or the like), diagnostic protocols, various body marks, and the like. For example, the storage 150 is implemented with a semiconductor memory element such as a RAM, a flash memory, and the like, a hard disk drive (HDD), an optical disk, or the like.

The data stored in the storage 150 can be transferred to an external device via the NW interface 160. Examples of external devices include a personal computer (PC) and tablet device used by physicians who perform image diagnosis, an image storage device that stores images, a printer, and the like, for example.

The NW interface 160 controls communications performed between the apparatus body 104 and external devices. Specifically, the NW interface 160 receives various information from external devices and outputs the received information to the processing circuitry 170. For example, the NW interface 160 is implemented with a network card, a network adapter, a network interface controller (NIC), and the like.

The processing circuitry 170 controls the entire processing of the ultrasonic diagnostic apparatus 100. Specifically, the processing circuitry 170 controls, based on various settings requests input from the operator via the input interface 102 and various control programs and various data read from the storage 150, the processing of the transmitting and receiving circuitry 110, the signal processing circuitry 130, and the image generation circuitry 140. The processing circuitry 170 also controls the display of ultrasonic images.

The processing circuitry 170 also performs an evaluation-value calculation function 171, the third beamforming function 172, and a weighting-factor input function 173. In this case, each of the processing functions of the evaluation-value calculation function 171, the third beamforming function 172, and the weighting-factor input function 173, which are constituent elements of the processing circuitry 170, is stored in the storage 150 in the form of computer programs executable by a computer, for example. The processing circuitry 170 is a processor. For example, the processing circuitry 170 reads the computer programs from the storage 150 and executes them to implement the function corresponding to each computer program. In other words, the processing circuitry 170 in a state at which each of the computer programs has been read out has each of the functions that are illustrated in the processing circuitry 170 in FIG. 1. In FIG. 1, the processing functions performed by the evaluation-value calculation function 171, the third beamforming function 172, and the weighting-factor input function 173 have been described as being implemented by a single processor, but the processing circuitry 170 may be configured by combining a plurality of independent processors and each processor may implement each function by executing the relevant computer program. In FIG. 1, a single storage 150 has been described to store the computer program corresponding to each of the processing functions, but a plurality of storage circuits may be arranged to be distributed and the processing circuitry 170 may be configured to read the corresponding computer programs from the individual storage circuits.

The term "processor" used in the above-described explanation refers to circuitry such as a central processing unit (CPU), a graphical processing unit (GPU) or an application-specific integrated circuit (ASIC), a programmable logic device (for example, simple-programmable logic device (SPLD) and complex-programmable logic device (CPLD)), a field-programmable gate array (FPGA), and the like, for example. The processor reads and executes the computer program stored in the storage 150 to implement the function. In place of storing the computer program in the storage 150, the computer program may be configured to be incorporated directly into the circuitry of the processor. In this case, the processor reads and executes the computer program incorporated in the circuitry to implement the function.

The ultrasonic diagnostic apparatus 100 utilizes adaptive beamforming based on the spatial correlation of reflected wave signals.

First, with reference to FIG. 3 and FIG. 4, the spatial correlation of reflected wave signals will be explained. The reflected wave signals output from the transducer elements 101*a* will be explained with reference to FIG. 3 and FIG. 4, and thereafter, the spatial correlation of the reflected wave signals will be explained.

Figure 3:
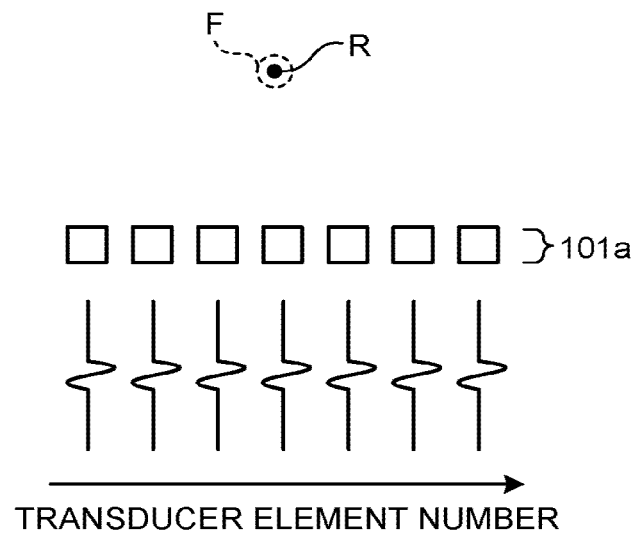
FIG. 3 is a diagram illustrating an example of reflected wave signals output from transducer elements when a reflector is present at the focal point where imaging is performed.

FIG. 3 is a diagram illustrating an example of the reflected wave signals output from the transducer elements 101*a* when the reflector R is present at the focal point F where imaging is performed. FIG. 4 is a diagram illustrating an example of reflected wave signals output from the transducer elements 101*a* when the reflector R is present at a position away from the focal point F where imaging is performed. In FIG. 3 and FIG. 4, the ultrasonic diagnostic apparatus 100 is assumed to generate an image of the focal point F. The reflector R illustrated in FIG. 3 and FIG. 4 is assumed to be sufficiently small relative to the ultrasonic wavelength.

Figure 4:
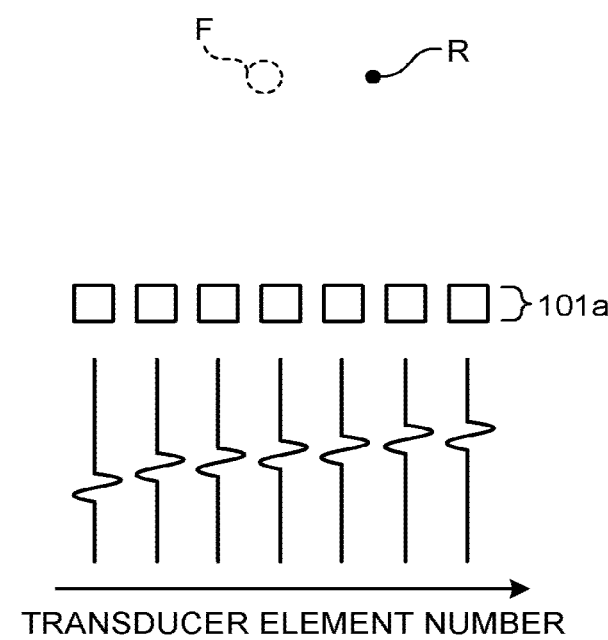
FIG. 4 is a diagram illustrating an example of reflected wave signals output from the transducer elements when a reflector is present at a position away from the focal point where imaging is performed.

As illustrated in FIG. 3 and FIG. 4, the distance from each transducer element 101*a* to the focal point F is different. Therefore, the ultrasonic diagnostic apparatus 100 gives a delay time according to the propagation time of a round trip of the ultrasonic wave from the transducer element 101*a* to the focal point F. This allows the ultrasonic diagnostic apparatus 100, as illustrated in FIG. 3, to acquire reflected wave signals for which the phase is matched among the reflected wave signals when the reflector R is present inside the focal point F. However, as illustrated in FIG. 4, when the reflector R away from the focal point F is present, the reflected wave reflected at the focal point F is affected by the reflected wave reflected by the reflector R. Accordingly, as illustrated in FIG. 4, the ultrasonic diagnostic apparatus 100 acquires reflected wave signals for which the phase varies among the reflected wave signals.

Next, the spatial correlation of reflected wave signals will be explained. When there is one reflector R, in the ultrasonic diagnostic apparatus 100, the phase of each reflected wave signal output from each transducer element 101*a* at the time position of the focal point F is substantially the same. Then, the ultrasonic diagnostic apparatus 100 determines that, when the phase of each reflected wave signal is substantially the same, the spatial correlation of the reflected wave signals is high.

Meanwhile, when there are two or more reflectors R, in the ultrasonic diagnostic apparatus 100, the phase varies among the reflected wave signals corresponding to each transducer element 101*a* at the time position of the focal point F. That is, the phases among the reflected wave signals are out of phase. Then, T the ultrasonic diagnostic apparatus 100 determines that, when the phase of each reflected wave signal varies, the spatial correlation of the reflected wave signals is low.

In this case, the second beamforming section 112 multiplies the amplitude of a plurality of reflected wave signals in adaptive beamforming in the DMAS method, and more adding is performed relative to the phase-additive method. Thus, when the phases among the reflected wave signals are in phase, the second beamforming section 112 outputs a large value as the result of the second beamforming processing. Meanwhile, when the phases among the reflected wave signals vary, the second beamforming section 112 outputs a small value as the result of the second beamforming processing, which is adaptive beamforming.

Thus, in adaptive beamforming, the second beamforming section 112 outputs a value that varies according to the spatial correlation of each reflected wave signal. In other words, the second beamforming section 112 outputs a value that varies according to the spatial correlation of the reflected wave signals. Thus, in the ultrasonic diagnostic apparatus 100, because the output for reflected waves from the point of interest at which the reflectors R are crowded varies, the contrast resolution and contrast-to-noise ratio with respect to such a point of interest may be degraded.

Meanwhile, the first beamforming section 111 performs the beamforming processing in the phase-additive method. In the beamforming processing in the phase-additive method, multiplying the amplitude of a plurality of reflected wave signals and increasing the number of times of adding are not performed. That is, the beamforming processing in the phase-additive method is less susceptible to the reflected waves from the reflectors R in the vicinity of the focal point F. Thus, in the first beamforming section 111, the processing result is less likely to vary relative to the second beamforming section 112, even when the spatial correlation of the reflected wave signals is low.

Therefore, the ultrasonic diagnostic apparatus 100 combines, according to the spatial correlation of the reflected wave signals, the processing result of the first beamforming section 111 and the processing result of the second beamforming section 112. This allows the ultrasonic diagnostic apparatus 100 to prevent the contrast resolution and contrast-to-noise ratio from degrading.

The evaluation-value calculation function 171 calculates an evaluation value indicating the spatial correlation of the reflected wave signals. In other words, the evaluation-value calculation function 171 calculates the evaluation value of the spatial correlation of the reflected wave signals received by the transducer elements 101*a*. The evaluation-value calculation function 171 is an example of a calculation section. The evaluation-value calculation function 171 performs the processing of calculating the evaluation value on the reflected wave data that is output from the transmitting and receiving circuitry 110 and for which no beamforming processing has been performed by the first beamforming section 111 or the second beamforming section 112.

In more detail, when the second beamforming section 112 performs the adaptive beamforming of the DMAS method (Non-Patent Literature 1) illustrated in FIG. 2, the evaluation-value calculation function 171 calculates the evaluation value w (t) expressed in the following Expression 3. The s (t) in Expression 3 represents the s (t) in Expression 1. N in Expression 3 indicates the total number of the transducer elements 101*a*.

$$w(t) = \frac{\left|\sum_n \hat{s}(t)\right|^2}{(N^2 - N)/2 \sum_n |\hat{s}(t)|^2} \quad (3)$$

The evaluation-value calculation function 171 also calculates an evaluation value for each pixel of the ultrasonic image. Then, the evaluation-value calculation function 171 performs the processing of calculating the evaluation value on the target region of the beamforming processing. Accordingly, the evaluation-value calculation function 171 generates a spatial correlation map in which the evaluation value is registered for each pixel in the target region of the beamforming processing. Regarding the method of calculating the evaluation value, in this case, Expression 3 has been used as an example, but the method is not limited to using such a post-multiplication signal and may be a method to evaluate the correlation among the transducer element received signals, such as the coherence-factor beamforming method, for example.

The evaluation-value calculation function 171 may, when calculating an evaluation value for speckles caused by the reflected waves reflected by the reflectors R, calculate an abnormal value. Therefore, the evaluation-value calculation function 171 may set a lower limit, by assuming uncorrelated reflected waves that have no correlation.

The third beamforming function 172 performs beamforming utilizing the processing result of adaptive beamforming. In more detail, the third beamforming function 172 performs the third beamforming processing, based on a first processing result that is the processing result of the first beamforming section 111, a second processing result that is the processing result of the second beamforming section 112, and the evaluation value calculated by the evaluation-value calculation function 171. The third beamforming function 172 is an example of a third beamforming section.

For example, the third beamforming function 172 combines, based on a combination ratio according to the evaluation value, the reflected wave data that is the first processing result with the reflected wave data that is the second processing result. In more detail, the third beamforming function 172 performs the processing expressed in the following Expression 4. The w (t) in Expression 4 is the evaluation value defined in Expression 3 and is an index that determines, in Expression 4, each weighting of the reflected wave data that is the first processing result and of the reflected wave data that is the second processing result. BF1(t) represents the reflected wave data that is the processing result of the first beamforming section 111. BF2(t) represents the reflected wave data that is the processing result of the second beamforming section 112. The α represents the parameter (adjustment parameter) for adjusting the weighting of BF1(t) and BF2(t).

$$BF_3(t) = (1 - w(t)^\alpha) BF_1(t) + w(t)^\alpha BF_2(t) \quad (4)$$

As illustrated in Expression 4, the third beamforming function 172 performs the third beamforming that, based on the combination ratio according to the evaluation value, combines the first processing result that is the processing result of the first beamforming section 111 and to which a weighting factor has been applied and the second processing result that is the processing result of the second beamforming section 112 and to which a weighting factor has been applied. That is, the third beamforming function 172 performs the third beamforming processing so that, when the evaluation value indicating the spatial correlation increases, the ratio of the second processing result that is the processing result of the second beamforming section 112 is increased. Then, the ultrasonic diagnostic apparatus 100 can, by changing the adjustment parameter for the weighting factor, change the weight in the evaluation value as desired. The $\alpha$ that is the adjustment parameter for the weighting factor in Expression 4 only needs to be proportional to w (t) that is the evaluation value, and it may be in the form of division such as w (t)/$\alpha$.

Then, the third beamforming function 172 causes the buffer memory 120 to store the processing result of the third beamforming processing. That is, the third beamforming function 172 causes the buffer memory 120 to store the reflected wave data for which the reflected wave data that is the first processing result and the reflected wave data that is the second processing result are combined.

The weighting-factor input function 173 receives inputs specifying the adjustment parameter for the weighting factor. The weighting-factor input function 173 is an example of an input section. For example, the weighting-factor input function 173 receives input specifying the adjustment parameter for the weighting factor from the input interface 102. Alternatively, the weighting-factor input function 173 receives input specifying the adjustment parameter for the weighting factor from the NW interface 160.

Next, the processing that the ultrasonic diagnostic apparatus 100 performs will be described.

FIG. 5 is a diagram illustrating an example of the beamforming processing performed by the ultrasonic diagnostic apparatus 100 according to the present embodiment.

The transmitting and receiving circuitry 110 generates ultrasonic data from the ultrasonic signals output from the transducer elements 101a that the ultrasonic probe 101 has (Step S1).

The first beamforming section 111 of the transmitting and receiving circuitry 110 performs the first beamforming processing on the ultrasonic data (Step S2). For example, the first beamforming section 111 performs the beamforming processing in the phase-additive method.

The second beamforming section 112 of the transmitting and receiving circuitry 110 performs the second beamforming processing on the ultrasonic data (Step S3). For example, the second beamforming section 112 performs the beamforming processing in the DMAS method.

The evaluation-value calculation function 171 performs, on the ultrasonic data, the processing of calculating the evaluation value of the spatial correlation of the reflected wave signals (Step S4).

The third beamforming function 172 performs the third beamforming processing based on the processing result of the first beamforming section 111, the processing result of the second beamforming section 112, and the evaluation value (Step S5). In more detail, the third beamforming function 172 performs the third beamforming processing that, based on the combination ratio according to the evaluation value, combines the processing result of the first beamforming section 111 and the processing result of the second beamforming section 112.

In this way, the ultrasonic diagnostic apparatus 100 completes the beamforming processing. Then, the ultrasonic diagnostic apparatus 100 generates an ultrasonic image from the reflected wave data that is the processing result of the third beamforming processing.

As in the foregoing, the ultrasonic diagnostic apparatus 100 can, by using the processing result for which the third beamforming processing has been performed, increase contrast resolution, and suppress amplitude variation. FIG. 6 is a diagram illustrating examples of the amplitude profile of an image generated by each beamforming processing. FIG. 6 illustrates the amplitude of the scanning lines of images of the phantom, for performance evaluation of the ultrasonic diagnostic apparatus 100, which have been captured using different beamforming processing. The (1) in FIG. 6 illustrates the amplitude of the scanning lines of the image captured using the first beamforming processing, that is, the beamforming processing in the phase-additive method. The (2) in FIG. 6 illustrates the amplitude of the scanning lines of the image captured using the second beamforming processing, that is, the beamforming processing in the DMAS method. The (3) in FIG. 6 illustrates the amplitude of the scanning lines of the image captured using the third beamforming processing.

The comparison target signal A1 in (1), the comparison target signal A2 in (2), and the comparison target signal A3 in (3) illustrated in FIG. 6 are compared. The width of the comparison target signal A2 is narrow relative to that of the comparison target signal A1. Then, the third beamforming function 172 performs the third beamforming processing that combines the processing result of the first beamforming processing and the processing result of the second beamforming processing. Thus, the width of the comparison target signal A3 is narrow relative to that of the comparison target signal A1. In other words, the image generated by the third beamforming processing is a sharper image. As in the foregoing, the third beamforming processing can enhance the contrast resolution.

Furthermore, the comparison target region B1 in (1), the comparison target region B2 in (2), and the comparison target region B3 in (3) illustrated in FIG. 6 are compared. The comparison target region B1 in (1), the comparison target region B2 in (2), and the comparison target region B3 in (3) illustrate the variation in the amplitude of the ultrasonic signal for which the reflected echo regions from a number of scatterers around the focal point F in the sub-wavelength region, that is, the reflected waves reflected by the reflectors R in the vicinity of the focal point F, have interfered with. The variation in the amplitude of the comparison target region B1 indicates about 38 dB, the variation in the amplitude of the comparison target region B2 indicates about 55 dB, and the variation in the amplitude of the comparison target region B3 indicates about 40 dB.

The third beamforming function 172 combines the processing result of the first beamforming processing and the processing result of the second beamforming processing. Therefore, the variation in the amplitude of the comparison target region B3 is greater than or equal to the variation in the amplitude of the comparison target region B1 but below the variation in the amplitude of the comparison target region B2. That is, the third beamforming processing can suppress the variation in amplitude due to interfering signals relative to the second beamforming processing.

As in the foregoing, the ultrasonic diagnostic apparatus 100 according to the present embodiment performs the first beamforming processing of the phase-additive method and the like and the second beamforming processing, which is adaptive beamforming of the DMAS method and the like. The ultrasonic diagnostic apparatus 100 further calculates an evaluation value of the spatial correlation of the reflected wave signals output from the transducer elements 101a. Then, the ultrasonic diagnostic apparatus 100 performs the third beamforming processing based on the processing result of the first beamforming processing, the processing result of the second beamforming processing, and the evaluation value.

As a result, the ultrasonic diagnostic apparatus 100 uses the processing result of the first beamforming processing of the phase-additive method and the like when the variation in the phase of each reflected wave signal output from the transducer elements 101a is large and uses the second beamforming processing that is adaptive beamforming when the variation in the phase of each reflected wave signal is small. Thus, the ultrasonic diagnostic apparatus 100 can utilize adaptive beamforming according to the spatial correlation of the reflected wave signals.

First Modification

In the present embodiment, it has been described that the third beamforming function 172 performs the third beamforming processing that, based on the combination ratio according to the evaluation value, combines the processing result of the first beamforming processing and the processing result of the second beamforming processing. However, the third beamforming function 172 is not limited to combining the processing results according to the evaluation value and may select the processing result according to the evaluation value.

The third beamforming function 172 performs the third beamforming that, based on the combination ratio according to the evaluation value, selects the first processing result, which is the processing result of the first beamforming section 111, or the second processing result, which is the processing result of the second beamforming section 112. For example, the third beamforming function 172 selects the result of the second beamforming processing when the evaluation value is higher than a threshold value and selects the result of the first beamforming processing when the evaluation value is lower than the threshold value. That is, the third beamforming function 172 selects the processing result of the second beamforming processing when the evaluation value of the spatial correlation of each of the reflected wave signals output from the transducer elements 101a is higher than the threshold value and selects the processing result of the first beamforming processing when the evaluation value of the spatial correlation of each of the reflected wave signals is lower than the threshold value. This allows the ultrasonic diagnostic apparatus 100 to utilize adaptive beamforming according to the spatial correlation of the reflected wave signals.

Second Modification

In the present embodiment, the first beamforming section 111 of the transmitting and receiving circuitry 110 performs the first beamforming processing. However, all or some of the functions that the first beamforming section 111 has may be performed by a computer program. That is, the processing circuitry 170 may, by executing the computer program, implement all or some of the functions that the first beamforming section 111 has. The second beamforming section 112 of the transmitting and receiving circuitry 110 performs the second beamforming processing. However, all or some of the functions that the second beamforming section 112 has may be performed by a computer program. That is, the processing circuitry 170 may, by executing the computer program, implement all or some of the functions that the second beamforming section 112 has.

It has been described that the evaluation-value calculation function 171 and the third beamforming function 172 are implemented by executing a computer program. However, all or some of the functions that the evaluation-value calculation function 171 and the third beamforming function 172 have may be implemented by hardware such as circuitry.

Third Modification

In the present embodiment, it has been described that the apparatus body 104 is provided with the first beamforming section 111, the second beamforming section 112, the evaluation-value calculation function 171, and the third beamforming function 172. However, the first beamforming section 111, the second beamforming section 112, the evaluation-value calculation function 171, and the third beamforming function 172 may be provided by the ultrasonic probe 101, not limited to the apparatus body 104.

Fourth Modification

In the present embodiment, it has been described that the ultrasonic diagnostic apparatus 100 is provided with the first beamforming section 111, the second beamforming section 112, the evaluation-value calculation function 171, and the third beamforming function 172. However, the first beamforming section 111, the second beamforming section 112, the evaluation-value calculation function 171, and the third beamforming function 172 may be provided by a computer device such as a server or workstation. For example, the ultrasonic diagnostic apparatus 100 transmits the reflected wave data generated by the transmitting and receiving circuitry 110 to the computer device via an interface such as the NW interface 160. The computer device may then perform various processing on the received reflected wave data by the first beamforming section 111, the second beamforming section 112, the evaluation-value calculation function 171, and the third beamforming function 172.

According to at least one of the foregoing embodiment and modifications, adaptive beamforming can be utilized according to the spatial correlation of reflected wave signals.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
transmitting and receiving circuitry configured to transmit and receive ultrasonic waves; and
processing circuitry, wherein
the transmitting and receiving circuitry is configured to
perform first beamforming processing on reflected wave signals output from a plurality of transducer elements configured to receive reflected waves, and
perform second beamforming processing different from the first beamforming processing on the reflected wave signals, and
the processing circuitry is configured to
calculate an evaluation value of spatial correlation of the reflected wave signals, and
perform third beamforming processing that combines a first processing result and a second processing result based on a combination ratio according to the evaluation value, the first processing result being a result of the first beamforming processing, the second processing result being a result of the second beamforming processing.

2. The ultrasonic diagnostic apparatus according to claim 1, wherein the processing circuitry is configured to perform the third beamforming processing such that the second processing result accounts for a larger ratio in a ratio between the first processing result and the second processing result as the evaluation value of the spatial correlation increases.

3. The ultrasonic diagnostic apparatus according to claim 1, wherein the processing circuitry is configured to perform the first beamforming processing in a phase-additive method by delaying the reflected wave signals corresponding to the reflected waves in accordance with a delay time from generation of the ultrasonic waves to reception of the reflected waves corresponding to the ultrasonic waves by each of the plurality of transducer elements and adding the delayed reflected wave signals together.

4. The ultrasonic diagnostic apparatus according to claim 1, wherein the processing circuitry is configured to perform the second beamforming processing by delaying each of the reflected wave signals corresponding to the reflected waves in accordance with a delay time from generation of the ultrasonic waves to reception of the reflected waves corresponding to the ultrasonic waves by each of the plurality of transducer elements and adjusting amplitude of the reflected wave signals output from a first transducer element by each of the reflected wave signals output from two or more second transducer elements different from the first transducer element, the first transducer element and the two or more second transducer elements being included in the plurality of transducer elements.

5. The ultrasonic diagnostic apparatus according to claim 4, wherein the processing circuitry is configured to perform the second beamforming processing in at least one of a delay-multiply-and-sum (DMAS) method, a minimum variance method, and a coherence factor beamforming method.

6. An ultrasonic diagnostic apparatus comprising:
  transmitting and receiving circuitry configured to transmit and receive ultrasonic waves; and
  processing circuitry, wherein
  the transmitting and receiving circuitry is configured to
    perform first beamforming processing on reflected wave signals output from a plurality of transducer elements configured to receive reflected waves, and
    perform second beamforming processing different from the first beamforming processing on the reflected wave signals, and
  the processing circuitry is configured to
    calculate an evaluation value of spatial correlation of the reflected wave signals, and
    perform third beamforming processing that, based on a combination ratio according to the evaluation value, combines a first processing result to which a weighting factor has been applied and a second processing result to which the weighting factor has been applied, the first processing result being a result of the first beamforming processing, the second processing result being a result of the second beamforming processing.

7. The ultrasonic diagnostic apparatus according to claim 6, wherein the processing circuitry is configured to receive an input of an adjustment parameter for the weighting factor.

8. An image processing apparatus comprising:
  processing circuitry
    configured to
      perform first beamforming processing on reflected wave signals output from a plurality of transducer elements configured to receive reflected waves,
      perform second beamforming processing different from the first beamforming processing on the reflected wave signals,
      calculate an evaluation value of spatial correlation of the reflected wave signals, and
      perform third beamforming processing that combines a first processing result and a second processing result based on a combination ratio according to the evaluation value, the first processing result being a result of the first beamforming processing, the second processing result being a result of the second beamforming processing.

* * * * *